United States Patent [19]

Linton et al.

[11] Patent Number: 4,634,667

[45] Date of Patent: Jan. 6, 1987

[54] PROCESS FOR PREPARING A HETEROPOLYSACCHARIDE, HETEROPOLYSACCHARIDE OBTAINED THEREBY, ITS USE, AND STRAIN NCIB 11883

[75] Inventors: John D. Linton, Sittingbourne; Michael W. Evans, Chichester; Andrew R. Godley, Sittingbourne, all of England

[73] Assignee: Shell Oil Company, Houston, Tex.

[21] Appl. No.: 653,627

[22] Filed: Sep. 24, 1984

[30] Foreign Application Priority Data

Sep. 22, 1983 [GB] United Kingdom ............... 8325445

[51] Int. Cl.[4] .............................................. C12P 19/04
[52] U.S. Cl. .................................... 435/101; 435/104; 435/253; 435/824
[58] Field of Search ................ 435/101, 104, 253, 824

[56] References Cited

U.S. PATENT DOCUMENTS 4,269,939  5/1981  Kang et al. .......................... 435/104

FOREIGN PATENT DOCUMENTS 3214953  10/1983  Fed. Rep. of Germany ...... 435/101

Primary Examiner—Charles F. Warren
Assistant Examiner—Rebecca L. Thompson

[57] ABSTRACT

Process for preparing a heteropolysaccharide from strain NCIB 11883 and use of the latter e.g. as viscosity modifier in an aqueous system such as completion fluids, work over fluids, stimulation fluids, and preferably in drilling fluids and use in connection with well-treatments, and enhanced oil recovery.

7 Claims, 2 Drawing Figures

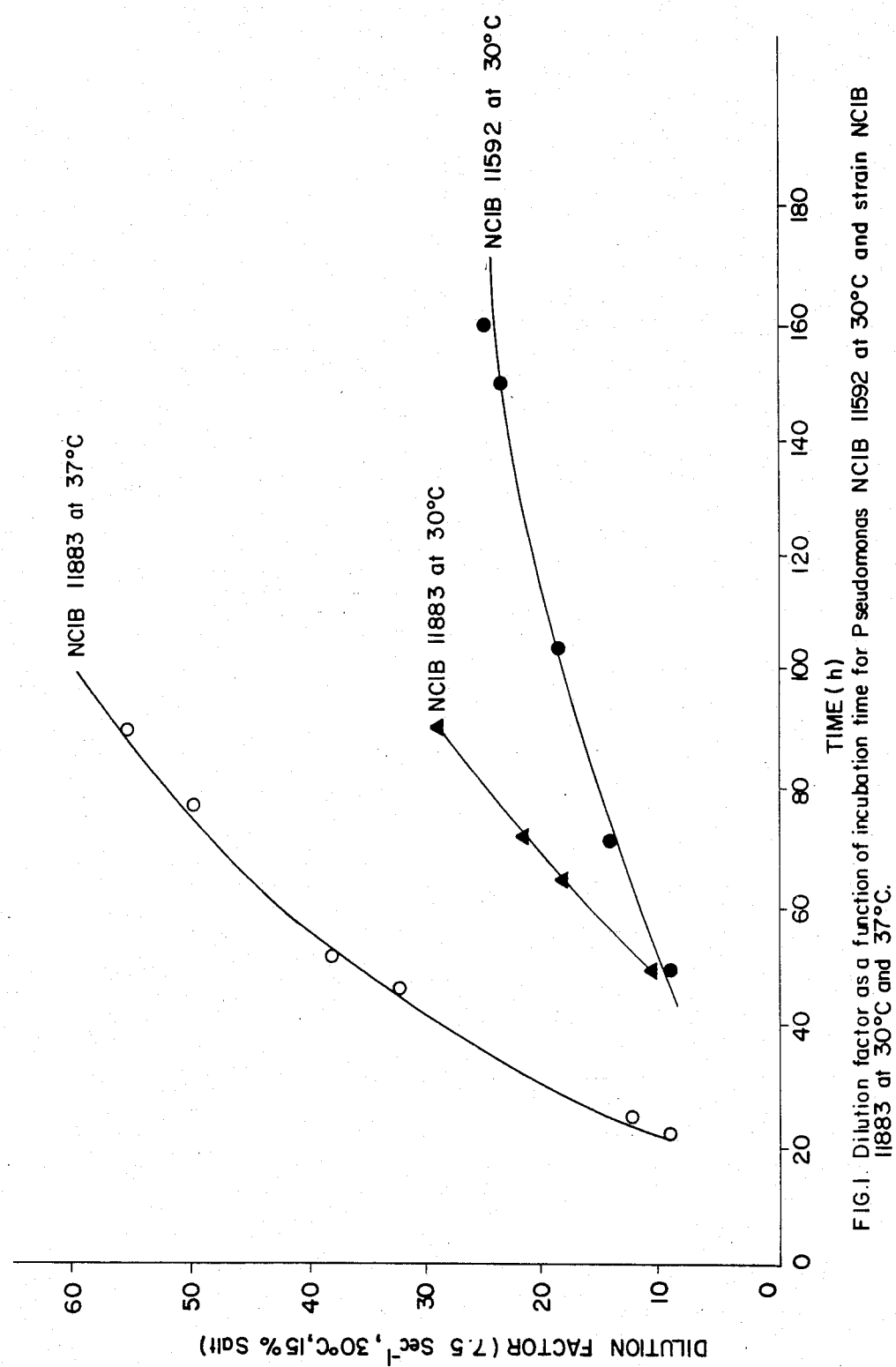
FIG. 1. Dilution factor as a function of incubation time for Pseudomonas NCIB 11592 at 30°C and strain NCIB 11883 at 30°C and 37°C.

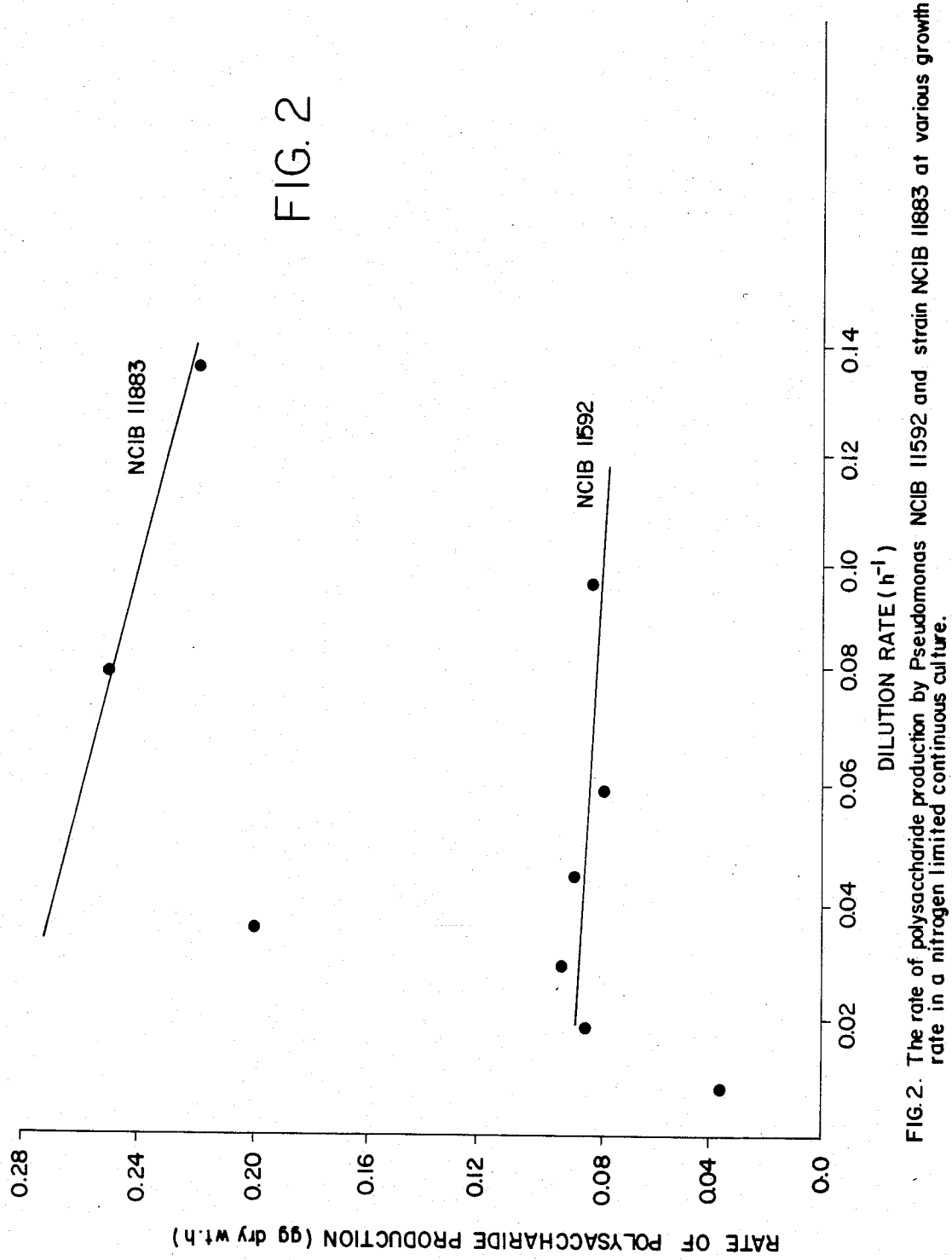
FIG. 2. The rate of polysaccharide production by Pseudomonas NCIB 11592 and strain NCIB 11883 at various growth rate in a nitrogen limited continuous culture.

PROCESS FOR PREPARING A HETEROPOLYSACCHARIDE, HETEROPOLYSACCHARIDE OBTAINED THEREBY, ITS USE, AND STRAIN NCIB 11883

The present invention relates to a process for preparing a heteropolysaccharide by fermenting a certain budding bacterium.

It is known that heteropolysaccharides can be prepared by subjecting a carbohydrate source to fermentation by certain micro-organisms such as Pseudomonas sp. NCIB 11592 as described in European Patent Application No. 81200479.4.

Applicants have now isolated a novel gram negative budding bacterium which has been deposited at the National Collection of Industrial Bacteria, Torry Research Station, Aberdeen, under accession number 11883. Compared with the microorganism Pseudomonas sp. NCIB 11592 the present microorganism NCIB 11883 appears to produce a polysaccharide at a considerably faster rate.

Furthermore the productivity in terms of visosifying power as expressed by the dilution factor of the culture broth (the extent to which the culture broth has to be diluted to give a solution with a viscosity of 20 cp at 30° C. in 15% salt at a shear rate of 7.5 $sec^{-1}$) is considerably higher in strain NCIB 11883 than in Pseudomonas sp. NCIB 11592. The present invention therefore provides a process for preparing a heteropolysaccharide which comprises growing the organism NCIB 11883 in an aqueous nutrient medium by aerobic fermentation of an assimilable carbohydrate and nitrogen source and recovering the heteropolysaccharide. The process may suitably be carried out as a batch-process, a fed-batch process with or without fill and draw or as a continuous process.

From productivity considerations a continuous process or a fill and draw process is preferred. Preferably the organism is grown in the absence of yeast extract in a chemically defined medium. More preferably the process is carried out under non-carbon source nutrient limitation conditions. The use of a chemically defined medium is advantageous since for a given productivity or for a given final cell concentration it appears easier to handle a nitrogen source such as sodium glutamate, ammonium or nitrate salts than complex nitrogen sources such as yeast extract or distillers dried solubles. The nitrogen source is preferably selected from the group consisting of sodium glutamate, ammonium-sulphate and sodium nitrate. The present invention further relates to the heteropolysaccharide as prepared by the process as hereinbefore described and to the use of the heteropolysaccharide as viscosity modifier in an aqueous solution. The present invention also relates to an aqueous system whenever thickened by the present heteropolysaccharide. Preferably the aqueous system belongs to the group consisting of completion fluids, work over fluids, stimulation fluids and drilling fluids. Stimulation fluids are used for e.g. hydraulic fracturing and acid fracturing. Most completion, work over, drilling and stimulation fluids contain at least one other additives e.g. salt (such as is conceivable in all brines), fluid loss additives, clay stabilizers, acids, bases, surfactants etc. The aqueous system to be thickened can however also be a printing ink or even a French dressing.

A drilling fluid comprising water and 0.06-1.5% by weight of the above heteropolysaccharide is a further preferred embodiment of the present invention. The present invention also encompasses a method of treating a well comprising the introduction into the well of an aqueous medium comprising water and 0.05-1.5% by weight of the above heteropolysaccharide. The aqueous medium is suitably a brine or fluid and may contain additives as desired. The present invention further provides the use in enhanced oil recovery (EOR) of an aqueous solution comprising the above heteropolysaccharide. Use in EOR can be for displacing a fluid through a well and/or a permeable subsurface formation communicating with the well, in mobility control as mobility buffer, e.g. in surfactant micellar flooding, use in profile control, to reduce water production, to reduce water/oil ratio etc. The present invention further relates to a biologically pure strain NCIB 11883. Strain NCIB 11883 is an unusual gram negative budding bacterium that does not seem to fit easily into any known taxonomic group. The microorganism has been characterised and identified by the National Collection of Industrial Bacteria.

Characterization and identification of NCIB 11883

Results

Tests were at 30° C. except as stated

Cell morphology

Small rods, parallel-sided or slightly tapered, straight, or slightly bent or curved. Bipolar phase-dark areas in older cultures (CM55, 30°, 8 days). Flagella are lateral; clumping of cells on the EM grids.

Colony morphology

CM55 48 hours: off-white, translucent to semi-opaque, entire, convert, smooth & shiney, 1 mm, colonies slightly mucoid until more polysaccharide produced on glucose containing media.

CM55 colonly size: 24 hours, 0.2 mm, 38 hours 1.5 mm.

CM3 48 hours: good growth, off-white, circular, entire, convex, smooth, shiney, slightly mucoid, 1.5 mm. CM3+1.0% glucose 60 hours: good growth, off-white, circular, edge slightly irregular smooth, shiny, mucoid, 2.5-3 mm.

| Carbon Source Utilization - compounds listed in the tables for Pseudomonas in Bergey's Manual of Determinative Bacteriology 1974 and in the order for Pseudomonas in R.Y. Stanier et al. (1966) J. Gen. Microbiol. 43 159 | | | | | | | | |
|---|---|---|---|---|---|---|---|---|
| MCIB 11883 | | | | | NCIB 11883 | | | |
| CSU Cluster 1 | CSU NCIB 9439 9440 | CSU | Acid O-F(2) | | CSU Cluster 1 | CSU NCIB 9439 9440 | CSU | Acid O-F |
| Carbohydrates and sugar derivatives | | | | Alcohol | | | | |
| | | | | Methanol* | − | − | − | |
| D-Ribose | | + | | Ethanol | − | − | + | |

-continued

Carbon Source Utilization - compounds listed in the tables for Pseudomonas in Bergey's Manual of Determinative Bacteriology 1974 and in the order for Pseudomonas in R.Y. Stanier et al. (1966) J. Gen. Microbiol. 43 159

| | MCIB 11883 | | | | | NCIB 11883 | | | |
|---|---|---|---|---|---|---|---|---|---|
| | CSU Cluster 1 | CSU NCIB 9439 9440 | CSU | Acid O-F[2] | | CSU Cluster 1 | CSU NCIB 9439 9440 | CSU | Acid O-F |
| D-Xylose | + | + | + | + | Geraniol | − | −d | | |
| L-Arabinose | ± | + | + | trace | Non-nitrogenous aromatic and other | | | | |
| L-Rhamnose | + | − | + | | cyclic compounds | | | | |
| L-Glucose | + | + | + | weak + | meta-Hydroxybenzoate | − | − | | |
| D-Frutose | + | + | + | weak + | para-Hydroxybenzoate | I 35 | − | − | |
| Sucrose | + | − | + | + | Testosterone | − | − | | |
| Trehalose | + | − | + | trace | Aliphatic amino acids | | | | |
| Cellobiose | + | − | + | + | β-Alanine | + | +(L−) | + | |
| 2-ketogluconate | | | | | L-Valine | + | − | − | |
| Saccharate | − | − | − | | L-Arginine[x] | + | +(DL−) | + | |
| Galactose | + | + | + | trace | Amino acids containing a ring structure | | | | |
| Mannose* | + | + | + | trace | Histidine | ± | +(L−) | + | |
| Lactose* | | | + | weak + | L-Tryptophan* | | | − | |
| Maltose* | + | d | + | wk +/− | Anthranilate* | | | − | |
| Melibiose* | | | | trace | Amines | | | | |
| Fatty acids | | | | | Benzylamine | | | − | |
| Acetate | + | − | + | | Tryptamine | − | − | | |
| Propionate | +d | − | + | | α-Amylamine | − | d− | | |
| Butyrate | | | | | Miscellaneous nitrogenous compounds | | | | |
| Dicarboxylic acids | | | | | Betaine | + | + | | |
| Malonate | − | − | − | | Pantothenate | | | | |
| Hydroxy acids | | | | | | | | | |
| D (−)-Tartrate | − | − | − | | | | | | |
| meso-Tartrate | | | − | | | | | | |
| DL-Hydroxybutyrate | | | − | | | | | | |
| DL-Lactate | + | + | + | | | | | | |
| Glycollate | | | − | | | | | | |
| Miscellaneous organic acids | | | | | | | | | |
| Levulinate | | d DC− | − | | | | | | |
| Citraconate | ± | − | − | | | | | | |
| Mesaconate | | | − | | | | | | |
| Sugar Poly alcohols and glycols | | | | | | | | | |
| Erythritol | − | − | − | | | | | | |
| Sorbitol | + | + | + | + | | | | | |
| meso-Inesitol | + | + | + | weak + | | | | | |
| Adonitol | − | −+ | + | + | | | | | |
| Propylene glycol | − | − | − | | | | | | |
| 2,3-Butylene glycol | − | +− | − | − | | | | | |
| Poly Sugar alcohols and glycols | | | | | | | | | |
| D-Mannitol* | + | + | + | −(trace?) | | | | | |
| Glycerol | + | + | + | −(trace?) | | | | | |

(1) CSU = Carbon Source Utilization (Growth from sole carbon source).
(2) Acid O − F = Acid production from O − F medium.
*Additional compound
[x]in place of DL−
NCIB 9439 Mycoplana dimorpha and NCIB 9440 M. bULLATA CSU results are taken from Green P.N. 1981 and Green and Bousfield 1982 (d = doubtful results). Similarly for cluster 1 ± = different results for different strains.

| Isolate | NCIB 11883 |
|---|---|
| °C. incubation | 30° |
| Pyocyanin | |
| Fluorescence | − |
| L-Arg CSU | + |
| Betaine CSU | |
| Glucose CSU | + (coherent pellicle) |
| Lactate CSU | + (no pellicle) |
| Acetate CSU | − (no pellicle) |
| Sensitivity (1 day) | |
| Penicillin G | 4 µg − |
| Streptomycin | 25 µg weak + |
| Chloramphen | 50 µg + |
| Tetracycline | 25 µg +++ |
| Novobiocin | 5 µg + |
| Polymyxin B | 25 µg weak + |
| 0/129 | |
| Levan | |
| Growth factor requirements | − |
| Urease Christiansen | + |
| Litmus milk | brown (reduced?) partially peptonised (doubtful result) 28 |
| Gas glucose | |
| ONPG | |
| Arg Moller | − |
| Lys moller | − |
| Orn Moller | − |
| $NO_3^-$ to $NO_2^-$ | − |
| $NO_3^-$ to $N_2$Gas | + |
| residual $NO_3^-$ | − |
| Gel stab 20° | −28 |
| Gel plate | −7 |
| Casein plate | −7 |
| Starch plate | −7 |
| Lecith egg-yolk plate | −7 |
| Lipase egg-yolk plate | −7 |
| $NH_3$ | +7 |
| Indole | −7 |
| $H_2S$ (TSI) | −7 |
| Lead acetate paper | weak +7 |
| MR | −7 |
| VP | −7 |
| Arg Thornley | −7 |
| CM3 Growth at °C. (air incubators except 4°) | |
| 5° | − |
| 30° | + |
| 37° | + |
| CM1 (water bath) | |
| 41° | weak + |
| 45° | − |
| CM3 pH adjusted growth at pH | |
| 3 | − |
| 5 | 3+ |
| 7.2 | 3+ |
| 8 | 3+ |
| 9 | 3+ |
| 10 | 3+ |
| Growth in NaCl | |
| 2% | 3+ |
| 2% | 3+ |
| 4% | 3+ |
| 5% | − |
| 3-ketolactose production (De Ley method) | − |

References
1. Bergey's Manual of Determinative Bacteriology, 8th edn. (1974). (R.E. Buchanan & N.E. Gibbons, eds.). Baltimore: Williams & Wilkins.
2. Cowan, S.J. & Steel, K.J. (1974). Manual for the Identification of Medical Bacteria, Cambridge University Press.

Selected Media and Methods

CM1 Oxoid CM1 nutrient broth
CM3 Oxoid CM3 nutrient agar
CM55 Oxoid CM55 Blood Agar Base Mineral base Palleroni & Doudoroff 1972 modified (PD) (A. Rev. Phytopathol 10, 73)

$Na_2HPO_4.12H_2O$: 6.0 g
$KH_2PO_4$: 2.4 g
$NH_4Cl$: 1.0 g
$MgSO_4.7H_2O$: 0.5 g
$FeCl_3.6H_2O$: 0.01 g
$CaCl_2.6H_2O$: 0.01 g
Deionized water: 1 liter
The pH will be 6.8
This was the basal medium for the carbon source utilization (CSU) tests.

PD mineral base+0.1% filter-sterilized glucose (PDG)

Gelatin Stabs

Nutrient Broth No. 2 (Oxoid): 2.5%
Gelatin (Difco): 12.0%

Gelatin Plates

Nutrient Agar Oxoid CM3: 2.8%
Gelatin: 1.0%

Milk Plates

Skim Milk (Difco) separately sterilized: 3%
Peptone (Difco): 0.1%
Beef Extract Lab-Lemco: 0.1%
NaCl: 0.5%
Agar: 1.5%
pH 7.4 before autoclaving.

Growth in presence of salt

Basal media containing NaCl at concentrations of 2, 3, 4 and 5% were prepared according to the method of Hayward & Hodgkiss (1961). Cultures were incubated for days.

Growth factor requirement test

Sub cultures were made by straight wire three times in PDG medium made with glass distilled water. Satisfactory growth was obtained in about 4 days indicating there was no absolute requirement for growth factors.

Carbon Source Utilization

PD medium with 0.1% filter-sterilized sole carbon sources were inoculated and incubated for 14 days.

Acid Production From Carbohydrates

The oxidation-fermentation medium of Hayward & Hodgkiss (1961) was supplemented with 1% filter-sterilized carbon sources. The tubes were inoculated and incubated for 14 days.

The National Collection of Industrial Bactria has come to the conclusion that NCIB 11883 should be considered to be a strain of *Agrobacterium radiobacter*. The isolate is atypical in not producing 3-ketolactose.

The present invention will now be further illustrated by the following Examples.

EXAMPLE 1

Polysaccharide Production by The Budding Bacterium NCIB 11883

Demonstrating polysaccharide production during active growth.

Medium Composition $gl^{-1}$

| -continued | | |
|---|---|---|
| (A) (NH4)2 SO4 | 0.75 | g |
| KH2PO4 | 0.75 | g |
| (B) MgSO4 7H2O | 0.4 | g |
| FeSO4 1 M soln. | 0.05 | ml |
| CaCl2 2H2O | 0.012 | g |
| IPP Trace Element Solution | 2.5 | ml |
| (C) Glucose | 20 | g |
| IPP Trace Element Stock Solution $gl^{-1}$ | | |
| CuSO4 5H2O | 0.249 | g |
| MnSO4 4H2O | 0.223 | g |
| ZnSO4 7H2O | 0.287 | g |
| CoCl2 6H2O | 0.118 | g |
| H3BO3 | 0.030 | g |
| Na2MoO4 2H2O | 0.124 | g |
| KI | 0.083 | g |

Components A, B and C were autoclaved separately and mixed on cooling.

A Biotec fermenter containing approximately 3.2 L of the above medium was seeded with a 10% inoculum of strain NCIB 11883 that has been previously grown at pH 6.8 in MOD-$D_2$ medium in shake-flask culture incubated at 30° C. on a rotary shaker for 24 h. The MOD-$D_2$ medium is specified below

| MOD $D_2$ Medium pH 6.8 | |
|---|---|
| Compound | Concentration $1^{-1}$ |
| glucose | as indicated |
| (NH4)2 SO4 | 3.0 g |
| Na2H PO4 | 3.0 g |
| KH2PO4 | 3.0 g |
| MgSO4 7H2O | 0.2 g |
| FeSO4 | 63.2 mg |
| CaCl 2H2O | 1.33 mg |
| ZnSO4 7H2O | 0.36 mg |
| CuSO4 5H2O | 0.32 mg |
| MnSO4 4H2O | 0.30 mg |
| CoCL2 6H2O | 0.36 mg |
| H3BO4 | 0.20 mg |
| Na2MoO4 2H2O | 0.60 mg |
| Oxoid purified agar L28 | 15.0 g |

The fermenter was maintained at 30° C., pH 6.8, stirred at 1000 rpm with 2, six blade Rushton impellers and continuously aerated with 1000 ml/min air. Extracellular polysaccharide was produced during exponential growth of strain NCIB 11883, this organism appears to exhibit polymer production, in two phases i.e. during growth and after growth has ceased.

Before growth has ceased 2.5 g/l (culture medium) biopolymer was produced at a cell density of 2.5 g microorganisms/l (culture medium) during fermentation in 12 hours. After growth ceased the final yield was 6.5 g/l at a cell density of 2.5 g microorganisms/l (culture medium) in a total fermentation time of 45 hours.

EXAMPLE 2

A comparison of the kinetics of heteropolysaccharide production between strain NCIB 11883 and Pseudomonas NCIB 11592 in a fermenter at 30° C. and 37° C. in batch culture after growth has ceased

| Medium | |
|---|---|
| KH2PO4 | 0.68 $gl^{-1}$ |
| MgSO4 7H2O | 0.49 $gl^{-1}$ |
| MnSO4 4H2O | 0.44 $mgl^{-1}$ |
| ZnSO4 7H2O | 0.57 $mgl^{-1}$ |
| H3BO3 | 0.06 $mgl^{-1}$ |
| Na2MoO4 2H2O | 0.24 $mgl^{-1}$ |
| -continued | |
| Medium | |
| (NH4)2 SO4 | 0.79 $gl^{-1}$ |
| CaCl2 2H2O | 7.05 $mgl^{-1}$ |
| CuSO4 5H2O | 0.25 $mgl^{-1}$ |
| CoCl2 6H2O | 0.23 $mgl^{-1}$ |
| KI | 0.16 $mgl^{-1}$ |
| FeSO4 7H2O | 14.0 $mgl^{-1}$ |
| Glucose | 25 $gl^{-1}$ |

The above medium is designed so that the nitrogen source is exhausted once a cell density of approximately 1.6 $gl^{-1}$ is reached. Consequently once this cell density is reached no further growth occurs, however polymer production continues after growth has ceased.

A Biotec fermenter containing 2.5l of the above medium was seeded with a 6% inoculum of strain NCIB 11883 or Pseudomonas NCIB 11592 grown for 16 h at 30° C. or 37° C. Air was sparged through the fermenter at 600 ml min$^{-1}$ and the stirrer speed was kept constant at 500 rpm. The stirrer had 2 Rushton impellers, each having 6 blades.

Specific polymer production rates of 0.137 $gg^{-1}h^{-1}$ at 30° C. and 0.13 $gg^{-1}h^{-1}$ at 37° C. were observed for strain NCIB 11883 compared to a maximum rate of 0.066 $gg^{-1}h^{-1}$ observed for Pseudomonas NCIB 11592. More importantly, as mentioned before, the productivity in terms of viscosifying power as expressed by the dilution factor is considerably higher in strain NCIB 11883. FIG. 1 shows that at a comparable cell density of 1.6 $gl^{-1}$, the fermentation time required to produce a broth with a dilution factor of 25 is reduced from 160 h with Pseudomonas 11592 to 80 h with NCIB 11883 grown at 30° C. and further reduced to 35 h with NCIB 11883 grown at 37° C.

Yields of polysaccharide and productivities of polymer production by Pseudomonas NCIB 11592 and NCIB 11883 are shown in Table 1.

TABLE 1

| Organism | Productivity (g polymer $l^{-1} h^{-1}$) | Productivity (Dilution factor $h^{-1}$) | Yield of Polymer $gg^{-1}$ glucose |
|---|---|---|---|
| Pseudomonas NCIB 11592 | 0.064 | 0.156 | 0.43 |
| Strain NCIB 11883 at 30° C. | 0.15 | 0.31 | 0.57 |
| Strain NCIB 11883 at 37° C. | 0.14 | 0.71 | 0.52 |

The characteristics of extracellular polysaccharide produced in batch culture at 30° C. and 37° C. are shown in Table 2.

TABLE 2

| | NCIB 11883 produced at 30° C. in batch culture | | NCIB 11883 produced at 37° C. in batch culture | |
|---|---|---|---|---|
| Salts solution %* | 15 | 15 | 15 | 15 |
| Temp. °C. | 30 | 60 | 30 | 60 |
| Viscosity of a 1 $gl^{-1}$ solution cP at 7.5 s$^{-1}$ | 61 | 51 | 150 | 145 |
| Viscosity of a 1 $gl^{-1}$ solution cP at 23 s$^{-1}$ | 32 | 27 | 60 | 58 |
| Dilution Factor 20 cP | 26.5 | 18.5 | 55 | 43 |

*15% NaCl + 1.5% CaCl2

Polymer characteristics of Pseudomonas NCIB 11592 produced at 30° C. in batch culture are shown in Table 3.

TABLE 3

| | | |
|---|---|---|
| Salt solution % | 15 | 15 |
| Temp. °C. | 30 | 60 |
| Viscosity of a 1 gl$^{-1}$ solution, cP at 7.5 s$^{-1}$ | 79 | 55 |
| Viscosity of a 1 gl$^{-1}$ solution, cP at 23 s$^{-1}$ | 41 | 32 |
| Dilution Factor 20 cP | 24.5 | 17.5 |

EXAMPLE 3

Exponential Fed-batch production of polysaccharide

The medium was formulated to support the growth of approximately 1.2 gl$^{-1}$ dry wt of strain NCIB 11883. Until this point is reached the organism grows at $\mu$max (0.31 h$^{-1}$). Further growth was controlled by feeding (NH$_4$)$_2$ SO$_4$ exponentially so that the growth rate of the organism could be controlled at a predetermined value. The exponential feed rate was computer controlled.

| | Medium gl$^{-1}$ | |
|---|---|---|
| (A) | (NH$_4$)$_2$ SO$_4$ | 0.6 g |
| | KH$_2$PO$_4$ | 0.75 g |
| (B) | MgSO$_4$ 7H$_2$O | 0.4 g |
| | FeSO$_4$ 1M | 0.05 ml |
| | CaCl$_2$ 2H$_2$O | 0.012 g |
| | IPP Trace Elements | 2.5 ml |
| (C) | Glucose | 20 g |

Parts A, B and C were sterilised separately by autoclaving and mixed when cold.

A Biotec fermenter containing 2.5 L of the above medium was inoculated with a 10% inoculum (24 h shake flask culture in MOD-D2 at 30° C., pH 6.8) of strain NCIB 11883. Growth proceeded exponentially at maximum growth rate until the cell density reached approximately 1.2 gl. dry wt. The ammonia level in the fermenter was monitored and the exponential ammonia feed was switched on when the (NH$_4$)$_2$ SO$_4$ concentration fell below 20 ppm. The feed rate was controlled to give an exponential growth rate of 0.064 h$^{-1}$. The fermentation time required to produce a broth containing 10 gl$^{-1}$ extracellular polysaccharide was approximately 28 h. The specific rate of the polymer production was 0.12 g polymer g$^{-1}$ dry wt. h$^{-1}$. The overall productivity observed was 0.35 g polysaccharide L$^{-1}$h$^{-1}$.

EXAMPLE 4

Continuous polysaccharide production by strain NCIB 11883

Medium

As used in Example 1.

Growth Conditions

Strain NCIB 11883 was grown under nitrogen limitation in a Biotec fermenter of working volume approximately 3.1 L. The temperature was maintained at 30° C. and the pH controlled at 6.8 by the addition of 2N NaOH+2N KOH. The fermenter was spraged with air at a rate of 1 L/min and continuously stirred with two Rushton impellers (6 blades each) at 1000 rpm. The organism was cultured at various growth rates and the kinetics of polymer production observed.

The rates of polysaccharide production of Pseudomonas 11592 and strain NCIB 11883 are compared in FIG. 2. Strain NCIB 11883 has a specific rate of polysaccharide production that is approximately 2-3 times faster than that of Pseudomonas 11592. Moreover the yield of polysaccharide per g glucose and oxygen consumed are also significantly higher in strain NCIB 11883 than in Pseudomonas 11592, as shown in Table 4.

A summary of the yields of polysaccharide production from glucose and oxygen, of cell production and the overall carbon balanced for each steady state under nitrogen limitation is shown in Table 4.

TABLE 4

A summary of yields and rates of polysaccharide production as a function of growth rate for a nitrogen limited culture of strain NCIB 11883. 30° C. pH 6.8

| | | | | |
|---|---|---|---|---|
| Dilution rate (h$^{-1}$) | 0.034 | 0.047 | 0.080 | 0.137 |
| Yield of Polysaccharide from glucose g dry wt g$^{-1}$ glucose | 0.519 | 0.60 | 0.55 | 0.287 |
| Yield of Cells from glucose g dry wt g$^{-1}$ glucose | 0.068 | 0.096 | 0.12 | 0.18 |
| Yield of Polymer from O$_2$ g dry wt g$^{-1}$ O$_2$ | 1.6 | 3.2 | 2.19 | 1.6 |
| Yields of cells from O$_2$ g dry wt g$^{-1}$ O$_2$ | 0.22 | 0.53 | 0.68 | 0.95 |
| Rate of glucose consumption g g$^{-1}$ dry wt h$^{-1}$ | 0.35 | 0.49 | 0.62 | 0.76 |
| Rate of polymer production g g$^{-1}$ dry wt h | 0.205 | 0.30 | 0.245 | 0.21 |
| g g$^{-1}$ crude protein h$^{-1}$ | 0.459 | 0.62 | 0.52 | |
| Carbon recovery | | | | |
| input | 100 | 100 | 100 | 100 |
| cell carbon | 8.8 | 10.5 | 14.02 | 19.7 |
| Polymer carbon | 48.7 | 62.4 | 44.0 | 33.5 |
| Other soluble products carbon | 31.6 | 7.35 | 22.9 | 38 |
| CO$_2$ carbon | 18.8 | 17.0 | 15.75 | 16.78 |
| Recovery % | — | 97.25 | 96.6 | — |
| Polymer conc. | | | | |
| direct dry wt | 9.17 | 9.84 (9.41) | 4.77 | 2.58 |
| IPA* precipitated dry wt. | 8.52 | 9.41 | 5.37 | 2.50 |

*IPA = isopropylalcohol

A summary of the maximum yields and rates observed for polymer production for Pseudomonas NCIB 11592 and strain NCIB 11883 grown under nitrogen limitation in continuous culture is given in Table 5.

TABLE 5

A comparison of the yields and rates of polysaccharide production between Pseudomonas NCIB 11592 and strain NCIB 11883 grown under nitrogen limitation in continuous culture, at 30° C., pH 6.8

| | | Maximum value for | |
|---|---|---|---|
| Parameter | Units | NCIB 11592 at D(h$^{-1}$) | NCIB 11883 at D(h$^{-1}$) |
| Specific rate of production | g g$^{-1}$ dry wt. h-1 | 0.9 (0.04) | 0.30 (0.047) |
| Volumetric polymer productivity | gl$^{-1}$ h$^{-1}$ dry wt. h-1 | 0.13 (0.03) | 0.46 (0.047) |
| Polymer yield on glucose | g (g glucose)$^{-1}$ | 0.4 (0.02) | 0.60 (0.047) |

TABLE 5-continued

A comparison of the yields and rates of polysaccharide production between Pseudomonas NCIB 11592 and strain NCIB 11883 grown under nitrogen limitation in continuous culture, at 30° C., pH 6.8

| Parameter | Units | Maximum value for NCIB 11592 at $D(h^{-1})$ | Maximum value for NCIB 11883 at $D(h^{-1})$ |
|---|---|---|---|
| Polymer yield on $O_2$ | $g\ g^{-1}\ O_2$ | 0.92 (0.03) | 3.2 (0.047) |
| Polymer to cell ratio | $g\ g^{-1}$ dry wt bacteria | 5.0 (0.017) | 6.3 (0.047) |
| | $g\ g^{-1}$ cell protein | 8.2 (0.020) | 12.8 (0.047) |

*Optimum dilution rate at which maximum parameter value was measured is given in brackets The characteristics of the polysaccharide produced by strain NCIB 11883 in continuous culture under nitrogen limitation at D=0.034 $h^{-1}$, 30° C., pH 6.8 are shown in Table 6.

TABLE 6

| | | | | | |
|---|---|---|---|---|---|
| Salt Solution % | 15% | 15% | 3% | 3% | 0% |
| Temp °C. | 30 | 60 | 30 | 60 | 30 |
| Viscosity of a 1 $gl^{-1}$ solution, cP at 7.5 $s^{-1}$ | 110 | 96 | 90 | 70 | 84 |
| Viscosity of a 1 $gl^{-1}$ solution, cP at 23 $s^{-1}$ | 50 | 45 | 42 | 35 | 38 |
| Dilution Factor 20 cP 7.5 $s^{-1}$ | 6.5 | 4.9 | 5.5 | 3.9 | 5.6 |
| D.F./$[P]^{dw}$ (R Factor) | 2.83 | 2.13 | 2.39 | 1.70 | 2.43 |
| Filtration 5 $\mu$M + PF* | 16.5 | 14.2 | 11.4 | 11.6 | 7.5 |
| Sequential 1.2 $\mu$M | 37.5 | 39 | 20.7 | 17.5 | 15.5 |
| Time for 200 ml 0.8 $\mu$M | 39.0 | 42.5 | 40 | 58.1 | 15.2 |

*prefilter

The characteristics of polysaccharide produced by strain NCIB 11883 under nitrogen limitation in continuous culture at D=0.05 $h^{-1}$, 37° C., pH 6.8 is shown in Table 7.

TABLE 7

| | | | |
|---|---|---|---|
| Salt Solution % | 0 | 3 | 15 |
| Temp °C. | 30 | 30 | 30 |
| Viscosity of a 1 $gl^{-1}$ solution, cP at 7.5 $s^{-1}$ | 135 | 138 | 130 |
| Viscosity of a 1 $gl^{-1}$ solution cP at 23 $s^{-1}$ | 56 | 58 | 54 |

Results of a chemical analysis of polysaccharide produced by strain NCIB 11883 are shown in Table 8.

TABLE 8

| | |
|---|---|
| Glucose: Galactose | 5:1–10:1 |
| Pyruvic acid % | 1.9–5.5 |
| Succinic acid % | 2.4–10.1 |

Additional acids present but not identified except traces of acetate.

We claim:
1. A process for preparing a heteropolysaccharide which comprises growing strain NCIB 11883 in an aqueous nutrient medium by aerobic fermentation of an assimilable carbohydrate and nitrogen source and recovering the heteropolysaccharide.
2. A process as claimed in claim 1 which is carried out as a continuous process or as a fill and draw process.
3. A process as claimed in claim 2 in which the organism is grown in the absence of yeast extract in a chemically defined medium as hereinbefore defined.
4. A process as claimed in claim 3 which is carried out under non-carbon source nutrient limitation conditions.
5. A process as claimed in claim 4 in which the nitrogen source is selected from the group consisting of sodium glutamate, ammonium sulphate and sodium nitrate.
6. Heteropolysaccharide as prepared by a process as claimed in any one of the claims 1-5.
7. A biologically pure culture of *Agrobacterium radiobacter*, NCIB 11883.

* * * * *